United States Patent
Locke et al.

(10) Patent No.: US 10,076,587 B2
(45) Date of Patent: Sep. 18, 2018

(54) PROTEASE MODULATING WOUND INTERFACE LAYER FOR USE WITH NEGATIVE PRESSURE WOUND THERAPY

(71) Applicant: KCI Licensing, Inc., San Antonio, TX (US)

(72) Inventors: Christopher Brian Locke, Bournemouth (GB); Timothy Mark Robinson, Basingstoke (GB); Breda Mary Cullen, Skipton (GB)

(73) Assignee: KCI Licensing, Inc., San Antonio, TX (US)

( * ) Notice: Subject to any disclaimer, the term of this patent is extended or adjusted under 35 U.S.C. 154(b) by 503 days.

(21) Appl. No.: 14/819,988

(22) Filed: Aug. 6, 2015

(65) Prior Publication Data
US 2016/0038626 A1 Feb. 11, 2016

Related U.S. Application Data

(60) Provisional application No. 62/035,880, filed on Aug. 11, 2014.

(51) Int. Cl.
| | | |
|---|---|---|
| *A61L 15/00* | (2006.01) | |
| *A61L 15/42* | (2006.01) | |
| *A61L 15/32* | (2006.01) | |
| *A61L 15/28* | (2006.01) | |
| *A61L 15/22* | (2006.01) | |
| *A61H 9/00* | (2006.01) | |

(52) U.S. Cl.
CPC ............ *A61L 15/42* (2013.01); *A61H 9/0057* (2013.01); *A61L 15/225* (2013.01); *A61L 15/28* (2013.01);
(Continued)

(58) Field of Classification Search
None
See application file for complete search history.

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

Huang, et al. "Engineered collagen-PEO nanofibers and fabrics", 2001 J. Biomater, Sci. Polymer Edn., vol. 12, No. 9, pp. 979-993.
(Continued)

*Primary Examiner* — Stephen R Crow

(57) ABSTRACT

Systems, methods, and apparatuses for modulating proteases including matrix metalloproteinase (MMP), elastase, and bacterial protease in a negative pressure therapy system are described. A mesh having a sacrificial substrate is included. The sacrificial substrate includes a plurality of collagen fibers reinforced with a supporting material and intersecting with each other to form a network of collagen fibers having a plurality openings. The openings of the plurality of openings have an average area between about 0.5 mm$^2$ and about 20 mm$^2$ to permit the flow of negative pressure through the mesh. The sacrificial substrate can also include oxidized regenerated cellulose.

25 Claims, 5 Drawing Sheets

(52) U.S. Cl.
CPC .......... *A61L 15/325* (2013.01); *A61L 15/425*
(2013.01); *A61L 2430/34* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Loco et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Goub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Mute |
| 4,392,858 A | 7/1983 | Goorgo et al. |
| 4,419,097 A | 12/1983 | Rowland |
| 4,465,485 A | 8/1984 | Kashrnor et al. |
| 4,475,909 A | 10/1984 | Esenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas |
| 4,569,348 A | 2/1986 | Hasskriger |
| 4,605,399 A | 8/1986 | Weston et al. |
| 4,608,041 A | 8/1986 | Nielsen |
| 4,640,688 A | 2/1987 | Hauser |
| 4,654,662 A | 3/1987 | Van Orsdel |
| 4,655,754 A | 4/1987 | Richmond et al. |
| 4,710,165 A | 12/1987 | McNeil et al. |
| 4,733,659 A | 3/1988 | Edenbaurn et al. |
| 4,743,232 A | 5/1988 | Kruger |
| 4,758,220 A | 7/1988 | Sunclblom et al. |
| 4,787,888 A | 11/1988 | Fox |
| 4,826,494 A | 6/1989 | Richmond |
| 4,838,883 A | 6/1989 | Matsuura |
| 4,840,187 A | 6/1989 | Brazier |
| 4,883,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kelt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Kararri et al. |
| 5,176,663 A | 1/1993 | Svedrnan et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | Debusk |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewaji |
| 5,607,388 A | 3/1997 | Ewall |
| 5,636,643 A * | 6/1997 | Argenta ............ A61M 1/0088 128/897 |
| 5,645,081 A | 7/1997 | Argenta et al. |
| 6,071,267 A * | 6/2000 | Zamierowski ...... A61F 13/0203 604/289 |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 9,402,940 B2 * | 8/2016 | Locke ................ A61M 1/0088 |
| 9,408,956 B2 * | 8/2016 | Zamierowski ...... A61M 1/0084 |
| 9,421,309 B2 * | 8/2016 | Robinson ............ A61M 1/0001 |
| 9,427,502 B2 * | 8/2016 | Robinson ............ A61M 1/0031 |
| 9,452,245 B2 * | 9/2016 | Jaeb ................... A61M 1/0088 |
| 9,452,246 B2 * | 9/2016 | Heaton ............... A61M 1/0088 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 201307997 A1 | 1/2013 |

OTHER PUBLICATIONS

International Search Report and Written Opinion for corresponding PCT Application No. PCT/2015/044024 dated Nov. 10, 2015.
Louis C. Argenta, MD and Michael J. Morykwas, PHD; Vacuum-Assisted Closure: A New Method for Wound Control and Treatment; Clinical Experience; Annals of Plastic Surgery.

(56) References Cited

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Wifflams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/the British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2400), 53, pp. 484-487.

George V. Letsou, MD., et al; "Stimulation of Adenylate Cyclase Activity in Cultured Endothelial Cells Subjected to Cyclic Stretch", Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, Vol, 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/G698/02713; dated Jun. 8, 1999.

Pot International Examination and Search Report, PCT International Application PCT/GB96/02802; dated Jan. 15, 1998 & Apr. 29, 1997.

PCT Written OpinIon, PCT International Application PCT/GB96/02802; dated Sept, 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgcal Management of Purulent Wounds"; Vestnik Khirurgi, Sep. 1986, pp. 18-21 and 6 page English translation thereof.

Davydov, Yu, A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English thereof translation.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Charmer, Mark E., M.D., et al; "Effective Management of incisional and cutaneous fistulae with closed suction wound drainage"; Contemporary Surgery, vol. 34, Jun. 1989, pp. 59-63.

Egnell Minor: Addition to the Users Manual Concerning Overflow Protection—Concerns all Egnell Pumps, Feb. 3, 1983 pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Egnell Minor, Instruction Book, First Edition, 300 7502, Feb. 1975, pp. 1-24.

* cited by examiner

PROTEASE MODULATING WOUND INTERFACE LAYER FOR USE WITH NEGATIVE PRESSURE WOUND THERAPY

The present invention claims the benefit, under 35 USC § 119(e), of the filing of U.S. Provisional Patent Application Ser. No. 62/035,880, entitled "Protease Modulating Wound Interface Layer for use with Negative Pressure Wound Therapy," by Locke et al., filed Aug. 11, 2014, which is incorporated herein by reference for all purposes.

TECHNICAL FIELD

The invention set forth in the appended claims relates generally to tissue treatment systems and more particularly, but without limitation, to a wound interface layer that modulates matrix metalloproteinase in a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with negative pressure may be commonly referred to as "negative-pressure therapy," but is also known by other names, including "negative-pressure wound therapy," "negative-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for modulating matrix metalloproteinase (MMPs) in a negative-pressure therapy environment are set forth in the appended claims. Illustrative embodiments are also provided to enable a person skilled in the art to make and use the claimed subject matter. For example, a mesh for modulating matrix metalloproteinase (MMP) in a negative pressure therapy system is described. The mesh may include a sacrificial substrate including a plurality of collagen fibers reinforced with a supporting material and intersecting with each other to form a network of collagen fibers having a plurality openings. The openings of the plurality of openings have an average area between about 0.2 mm$^2$ and about 20 mm$^2$ to permit the flow of negative pressure through the mesh.

Alternatively, other example embodiments describe a negative-pressure therapy system for modulating matrix metalloproteinase (MMP) in a tissue site. The system includes a modulating layer including a plurality of collagen fibers reinforced with a supporting material and intersecting with each other to form a network of collagen fibers having a plurality openings. The openings of the plurality of openings have an average area between about 0.2 mm$^2$ and about 20 mm$^2$ to permit the flow of negative pressure through the mesh. The system may also include a manifold configured to be positioned adjacent the network and a cover configured to be positioned over the manifold and the network and coupled to tissue adjacent the tissue site to form a sealed space. A negative-pressure source may be configured to be fluidly coupled to the manifold to provide negative pressure to the sealed space through the manifold and the network.

In other embodiments, a method for manufacturing an apparatus for modulating matrix metalloproteinase (MMP) in a tissue site in a negative-pressure therapy environment is described. A plurality of collagen fibers reinforced with a supporting material may be formed, and a sacrificial substrate having the plurality of collagen fibers may be formed from the collagen fibers. The plurality of collagen fibers may be coupled to each other at intersections with each other to form a network of collagen fibers having a plurality openings. The openings of the plurality of openings have an average area between about 0.2 mm$^2$ and about 20 mm$^2$ to permit the flow of negative pressure through the mesh.

In still further embodiments, a method for providing negative-pressure therapy and modulating matrix metalloproteinase (MMP) in a tissue site is described. A sacrificial network may be provided that includes a plurality of collagen fibers reinforced with a supporting material and intersecting with each other to form a plurality openings. The openings of the plurality of openings have an average area between about 0.2 mm$^2$ and about 20 mm$^2$ to permit the flow of negative pressure through the mesh. The sacrificial network may be positioned adjacent to the tissue site, and a manifold may be positioned adjacent to the sacrificial network. A negative-pressure source may be fluidly coupled to the manifold, and negative pressure may be provided to the tissue site through the manifold and the sacrificial network.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of embodiments provides information that enables a person skilled in the art to make and use the subject matter set forth in the appended claims, but may omit certain details already well-known in the art. The following detailed description is, therefore, to be taken as illustrative and not limiting.

The embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
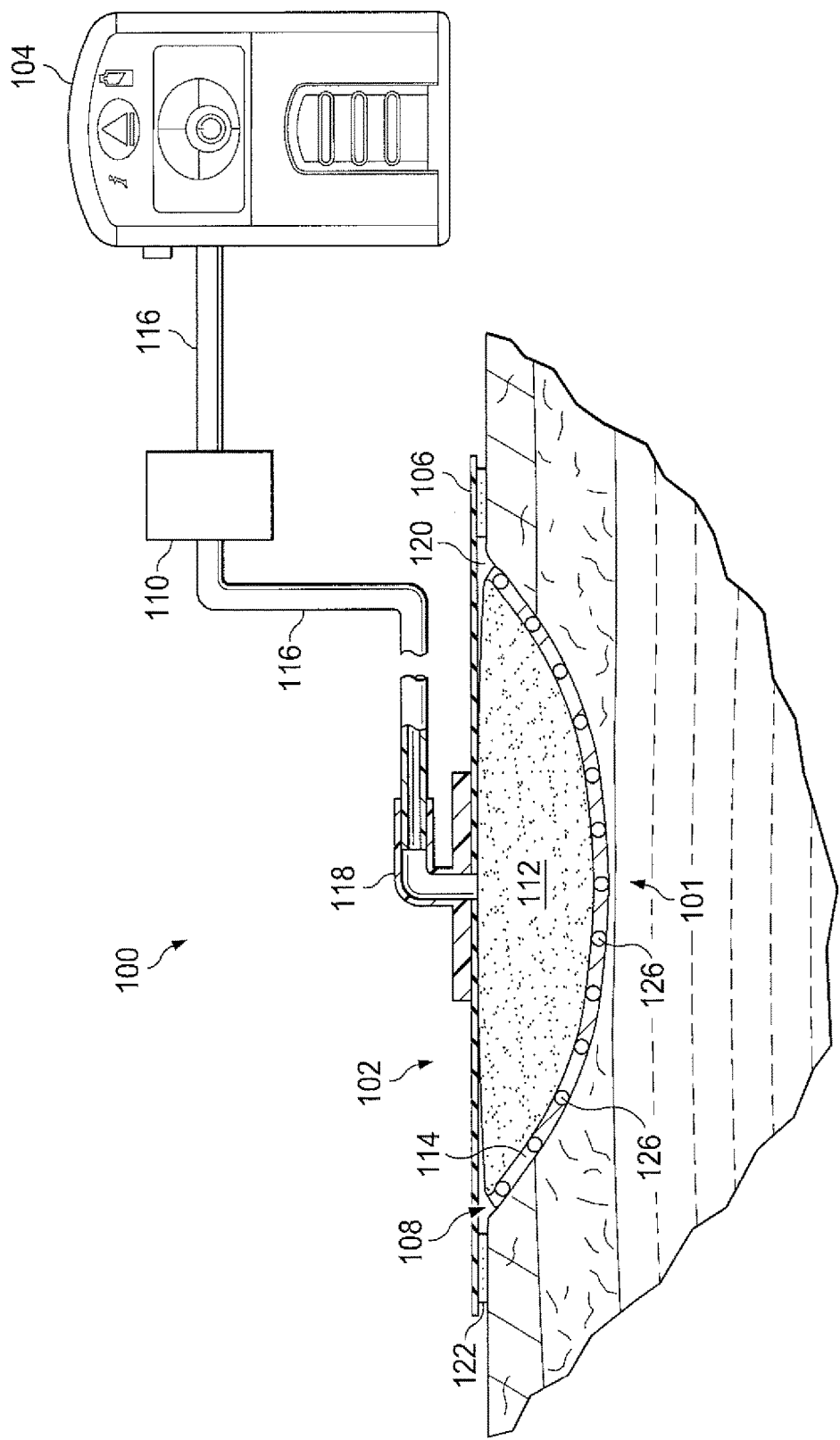
FIG. 1 is a sectional view, with a portion show in elevation of an example embodiment of a negative-pressure therapy system that can modulate matrix metalloproteinase in accordance with this specification.

FIG. 1 is sectional view, with a portion shown in elevation, of a negative-pressure therapy system 100 that can provide modulating agents to matrix metalloproteinase (MMP) at a tissue site 101 in accordance with this specification. The negative-pressure therapy system 100 may include a dressing and a negative-pressure source. For example, a dressing 102 may be fluidly coupled to a negative-pressure source 104, as illustrated in FIG. 1. A dressing may generally include a cover and a tissue interface. The dressing 102, for example, includes a cover 106 and a tissue interface 108. In some embodiments, the tissue interface 108 may include a manifold 112 and a mesh 114 that includes a plurality of collagen fibers 126. The negative-pressure therapy system 100 may also include a fluid container, such as a container 110, coupled to the dressing 102 and to the negative-pressure source 104.

In general, components of the negative-pressure therapy system 100 may be coupled directly or indirectly. For example, the negative-pressure source 104 may be directly coupled to the container 110 and indirectly coupled to the dressing 102 through the container 110. Components may be fluidly coupled to each other to provide a path for transferring fluids (i.e., liquid and/or gas) between the components.

In some embodiments, for example, components may be fluidly coupled through a tube, such as a tube 116, for example. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The dressing 102 may be fluidly coupled to the container 110 through the tube 116 and a connector, such as a connector 118. For example, the connector 118 may be a T.R.A.C.® Pad or Sensa T.R.A.C.® Pad available from KCI of San Antonio, Tex. In some embodiments, the connector 118 may be a portion of the tube 116 extending into a sealed therapeutic environment or may be a vacuum port on a micro-pump that extends into the sealed therapeutic environment.

In operation, the tissue interface 108 may be placed within, over, on, adjacent, or otherwise proximate to a tissue site. The cover 106 may be placed over the tissue interface 108 and sealed to tissue near the tissue site 101. For example, the cover 106 may be sealed to undamaged epidermis peripheral to the tissue site 101. Thus, the dressing 102 can provide a sealed therapeutic environment 120 proximate to the tissue site 101, substantially isolated from the external environment, and the negative-pressure source 104 can reduce the pressure in the sealed therapeutic environment 120. Negative pressure applied across the tissue site 101 through the tissue interface 108 in the sealed therapeutic environment 120 can induce macrostrain and microstrain in the tissue site 101, as well as remove exudates and other fluids from the tissue site 101, which can be collected in the container 110 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically refers to a position in a fluid path relatively closer to a negative-pressure source. Conversely, the term "upstream" refers to a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure. An ambient pressure may be the pressure in a local environment external to the sealed therapeutic environment 120 provided by the dressing 102. In many cases, the local ambient pressure may also be the atmospheric pressure at which a tissue site is located. Alternatively, negative pressure may be a pressure that is less than a hydrostatic pressure associated with tissue at the tissue site 101. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 108 can be generally adapted to contact the tissue site 101. The tissue interface 108 may be partially or fully in contact with the tissue site 101. If the tissue site 101 is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of the tissue site 101. For example, the size and shape of the tissue interface 108 may be adapted to the contours of deep and irregular shaped tissue sites.

In some embodiments, the tissue interface 108 may be a manifold, such as the manifold 112. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. In some illustrative embodiments, a manifold may have pores with a diameter in the range of about 20 microns to about 400 microns. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 108 may be made from a hydrophilic material, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment 120 is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLAVGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. In some example embodiments, the cover 106 may be a polymer drape, such as a polyurethane film, that is permeable to water vapor but impermeable to liquid. Such drapes typically have a thickness in the range of about 25 to about 50 microns. For permeable materials, the permeability generally should be low enough that a desired negative pressure may be maintained.

An attachment device, such as an attachment device 122, may be used to attach the cover 106 to an attachment surface, such as undamaged epidermis, a gasket, or another cover. The attachment device 122 may take many forms. For example, the attachment device 122 may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 g.s.m. Thicker adhesives, or combinations of adhesives, may be applied in some embodiments to improve the seal and reduce leaks. Other example embodiments of the attachment device 122 may include a double-sided tape, paste, hydrocolloid, hydrogel, silicone gel, or organogel.

The container 110 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

During healing of a tissue site, matrix metalloproteinase (MMP) is produced. MMPs are an enzyme that aids the process of remodeling a tissue site. MMPs may be classified as zinc-dependent endopeptidases that belong to a larger family of proteases that may be known as the metzincin superfamily. MMPs may be associated with both physiological and pathological processes, including morphogenesis, angiogenesis, tissue repair, cirrhosis, arthritis, and metastasis. Generally, MMPs degrade extracellular matrix proteins. Extracellular matrix proteins are extracellular components of a multicellular structure. Extracellular matrix proteins can support tissue, separate tissues, regulate communication between the cells of tissues, and regulate the dynamic behavior of cells. Extracellular matrix proteins can also store cellular growth factors that can be released when tissue is damaged. Extracellular matrix proteins aid in regrowth and healing of tissue by preventing the immune system response at the injury to prevent inflammation. Extracellular matrix proteins can also aid the surrounding tissue to repair the damaged tissue rather than form scar tissue. MMPs assist the extracellular matrix proteins in tissue healing by breaking down damaged extracellular matrix proteins when tissue is injured. Breaking down damaged extracellular matrix proteins allows undamaged extracellular matrix proteins to integrate with newly formed components. MMPs also remove bioflims that can cause infection, help establish new blood vessels in damaged tissue, aid in the migration of epithelial cells, and remodel scarred tissue. However, MMPs can inhibit healing of damaged tissue. For example, MMPs in the wrong locations in a tissue site or too many MMPs in a tissue site can degrade extracellular matrix proteins that are needed for healing. Typically, tissue sites that exhibit an increased inflammatory response may be producing MMPs at rates that can lead to inhibition of healing. Inflammation can also cause an increased production of fluid from the tissue site, leading to maceration and other degenerative conditions that may prolong healing time.

Excess MMPs may be modulated by adding modulating agents to the tissue site. A modulating agent may be an agent, such as a structural protein, that is added to the tissue site. Modulating agents may include scavenging or sacrificial structures formed from a protein material. If the sacrificial structure is placed adjacent a tissue site, the excess MMPs degrade the sacrificial structure rather than newly formed tissue, reducing existing inflammation and the likelihood of additional inflammation. Some sacrificial structures may include sheets of a collagen material that form a collagen substrate. The collagen substrate may be placed on a surface of a tissue site or coated onto another substrate, such as a tissue interface or manifold. Generally, a modulating agent should be placed in close contact to areas of a tissue site where the MMPs are active and deleterious to healing.

Some tissues sites may stall during healing. A stalled tissue site may be a tissue site that does not follow the desired healing progression within the desired time frame. A stalled tissue site may be caused by excess MMPs as well as excess elastases and bacterial proteases. Elastase and bacterial proteases are types of proteases that may aid in breaking down proteins. Excess elastase and bacterial proteases may inhibit healing by breaking down the new tissue as it develops, preventing the tissue site from healing. Similar to MMPs, elastases and bacterial proteases may be modulated by adding modulating agents, such as oxidized regenerated cellulose (ORC), to the tissue site. The ORC may be stable below a pH of about 4.4 and negatively charged. If the ORC is placed in the tissue site, the tissue site may react to raise the pH of the ORC to the natural pH of the body, producing glucuronic acid that may aid in the removal of undesired products from the tissue site. The ORC, being negatively charged, may also attract and bind with elastase and bacterial proteases, which are positively charged.

Application of negative-pressure therapy may encourage granulation and manage wound fluid, enhancing the effectiveness of the modulating agents. However, most modulating agents, such as a collagen substrate, are continuous and non-porous. If a collagen substrate, an ORC substrate, or a combined collagen/ORC substrate is placed adjacent to a tissue site so that the substrate is in close contact with the proteases, such as MMPs, elastases, and bacterial proteases of the tissue site, the substrate may act as a barrier to the flow of fluids, including negative pressure, Consequently, modulating agents can inhibit the transmission of negative pressure to a tissue site, preventing the negative-pressure therapy from encouraging granulation and managing wound fluids. Thus, while modulating agents may decrease damage caused by MMPs, elastases, and bacterial proteases, the modulating agents may increase maceration, limit granulation, and otherwise stymie the positive benefits of negative-pressure therapy. For at least this reason, clinicians are reluctant to use modulating agents with negative-pressure therapy. Although perforating a substrate to form holes in the substrate would help to transmit negative pressure to a tissue site, the material punched from the holes would be discarded as waste, which is not cost effective. Even if a sacrificial substrate is perforated, such substrate must also have holes of sufficient diameter to permit the flow of negative pressure and sufficient stiffness and strength to withstand the transmission of negative pressure to the tissue site.

These limitations and others may be addressed by the negative-pressure therapy system 100 that can provide a modulating agent for proteases including MMPs, elastases, and bacterial proteases while providing negative pressure to a tissue site. In some embodiments, the negative-pressure therapy system 100 may include a dressing 102 having a mesh 114 that includes a plurality of collagen fibers intersecting with each other to form a network having a plurality of openings of sufficient size or diameter to permit the flow of negative pressure through the mesh 114 that functions as the sacrificial substrate, sacrificial network, or modulating layer. The openings may be of any shape, but of sufficient size or area so as not to inhibit the flow of negative pressure. The collagen fibers may be reinforced by a supporting material wherein the collagen content of the collagen fibers may be about 30% of the total content of the collagen fibers. In other embodiments, the total collagen content of the collagen fibers may be between about 10% and about 50% of the total content of the collagen fibers. In some embodiments, the supporting material may be polyethylene oxide, and the polyethylene oxide may be between about 90% and about 50% of the total material content of the collagen fibers. The supporting material may be water soluble. The supporting material may also be biodegradable. In some embodiments, the supporting material may take the form of supporting fibers formed from the supporting material and twisted together with the collagen fibers to further reinforce the collagen fibers. In some embodiments, the mesh 114 may include fibers formed from ORC.

Figure 2:
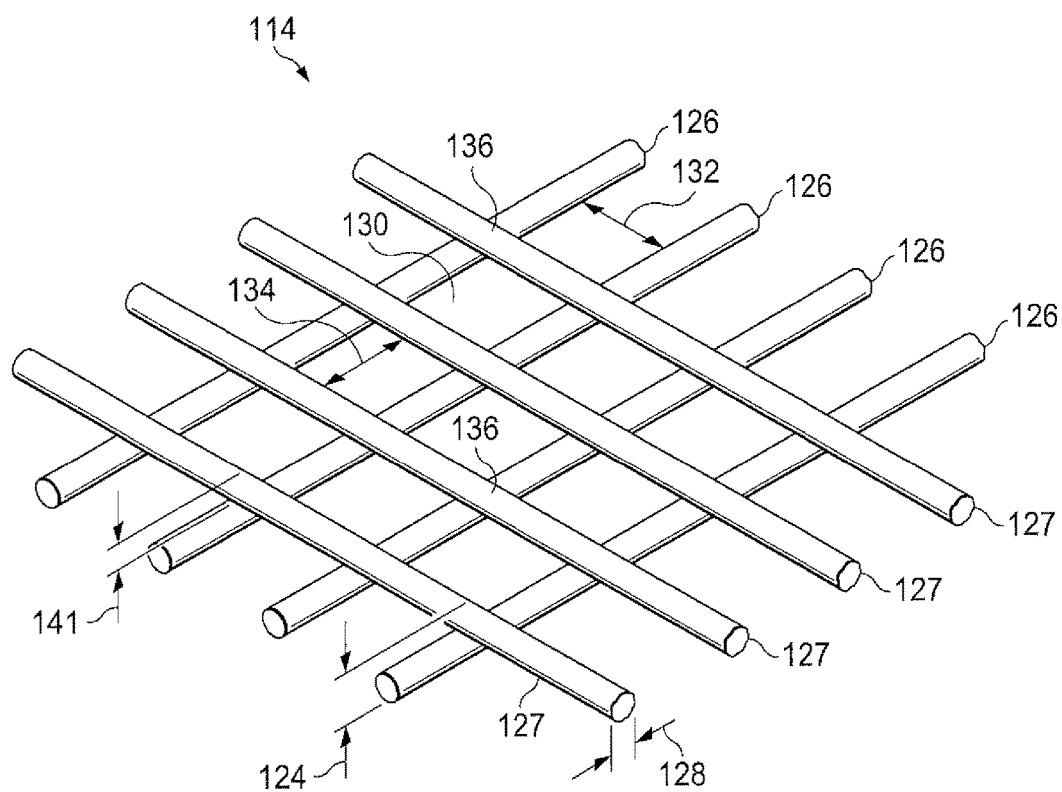
FIG. 2 is a perspective view, illustrating additional details that may be associated with a mesh of the negative-pressure therapy system of FIG. 1.

FIG. 2 is a perspective view of a portion of the mesh 114 that illustrates additional details that may be associated with some example embodiments of the negative-pressure therapy system 100 wherein the mesh 114 is formed from a plurality of collagen fibers 126, 127. In some embodiments, the mesh 114 may be formed by weaving, knitting, knotting, linking, or otherwise connecting the collagen fibers 126, 127 to form a regular pattern of openings or mesh apertures 130. As illustrated in FIG. 2, the mesh 114 may comprise a first plurality of collagen fibers 126 aligned substantially parallel to each other and a second plurality of collagen fibers 127 also aligned substantially parallel to each other, wherein the first and second plurality of collagen fibers 126, 127 are positioned adjacent to each other at an angle. Consequently, the first and second plurality of collagen fibers 126, 127 overlap each other to form a network having the plurality of openings or mesh apertures 130, The first and second plurality of collagen fibers 126, 127 intersect with each other to form a plurality of intersections 136. An intersection 136 of at least two collagen fibers 126, 127 may be formed by overlapping fibers or other types of connections between the fibers at an intersection 136.

The first and second plurality of collagen fibers 126, 127 may be separated from adjacent collagen fibers 126, 127, respectively, by a distance 132 and 134, respectively, which may be between about 0.5 mm and about 5 mm. In other embodiments, the distance 132 and 134 which may be between about 1.0 mm and about 2.5 mm. In some embodiments, the first direction of the distance 132 and the second direction of the distance 134 may be perpendicular. In some embodiments, the distance 132 and the distance 134 may be the same. In other embodiments, the angle foamed by the first direction of the distance 132 and the second direction of the distance 134 may be angles other than perpendicular, and the distance 132 and the distance 134 may not be the same.

In some embodiments, the mesh apertures 130 may have an average effective diameter of about 1 mm. An effective diameter of a non-circular area may be a diameter of a circular area having the same surface area as the non-circular area. For example, the surface area of a mesh aperture 130 where the distance 132 is 0.5 mm and the distance 134 is 0.5 mm may be 0.25 $mm^2$. The diameter of a circular area having a 0.25 $mm^2$ surface area is about 0.56 mm; consequently, the effective diameter of the exemplary mesh aperture 130 is about 0.56 mm. Similarly, if the distance 132 is about 4 mm and the distance 134 is about 4 mm, the effective diameter of the mesh aperture 130 may be about 4.51 mm. In some embodiments, each mesh aperture 130 may have an area formed by the effective diameter of the mesh aperture 130. In some embodiments, each mesh aperture 130 may be uniform in area. In other embodiments, each mesh aperture 130 may not be uniform in area. If the mesh apertures 130 are not uniform in area, the average of the areas of the mesh apertures 130 may be between about 0.2 $mm^2$ and about 20 $mm^2$. In some embodiments, the mesh apertures 130 may be square. In other embodiments, the mesh apertures 130 may form other shapes, such as rectangular, triangular, circular, ovular, or amorphous shapes.

In some embodiments, each of the collagen fibers 126, 127 may have a diameter 128. In some embodiments, the diameter 128 may be no greater than about 1 mm. In some embodiments, the diameter 128 may be about 1 micron. In some embodiments, the diameter 128 may be between about 5 microns and about 50 microns. The intersections 136 may have a prominence 141. In some embodiments, the prominence 141 at the intersections 136 may be equal to the diameter 128 of the collagen fibers 126, 127. In some embodiments, the prominence 141 may be reduced by compressing the mesh 114 following formation of the mesh 114. The prominences 141 may also be reduced by passing the mesh 114 through a calender, which may apply pressure to the mesh 114 to smooth out the mesh 114. In some embodiments, the prominence 141 may be less than about 1 mm.

In some embodiments, the mesh 114 may be substantially flat. For example, the mesh 114 may have a thickness 124, and individual portions of the mesh 114 may have a minimal tolerance from the thickness 124. In some embodiments, the thickness 124 of the mesh 114 may be based in part on the diameter 128 of the fibers 126, 127. In some embodiments, the thickness 124 of the mesh 114 may be about 1 mm, and the tolerance of the thickness 124 may be less than about 2 mm. In another exemplary embodiment, a tolerance of the thickness 124 of the mesh 114 may be less than about 1 mm. In other embodiments, a tolerance of the thickness 124 of the mesh 114 may be less than about 0.5 mm. In other embodiments, the thickness 124 of the mesh 114 may be between about 5 microns and about 50 microns.

In some embodiments, the mesh 114 may be formed by an extrusion process. For example, collagen may be blended with a polymer, such as poly (lactide-glycolide) or PLGA copolymers that may be particularly well-suited for the extrusion process. The blended collagen polymer may be extruded into the mesh 114 having the plurality of collagen fibers 126, 127 with the plurality of mesh apertures 130 formed between them.

In some embodiments, the collagen fibers 126, 127 may be formed from a plurality of staple fibers. A staple fiber may be a fiber of a selected standardized length. The collagen fibers 126, 127 may be a combination of staple fibers formed from collagen and staple fibers formed from a supporting material to reinforce the collagen material of the staple fibers of collagen. The staple fibers of collagen may be formed by melt spinning, wet spinning, electrospinning, or other suitable processes. Melt spinning may involve melting a collagen in a polymer and squeezing the combined substance through a spinneret to form the fiber. For example, collagen split skins may be denatured and dried, ground to a power on a centrifugal mill, and mixed with glycerol and deionized water. The solution may be fed into an extruder spinning system to form fibers. Wet spinning may involve dissolving the collagen in a polymer to form a coagulating bath having a low pH. Liquid in the coagulating bath may be evaporated to form a fine fiber. For example, a collagen dispersion may be prepared using an alkaline treated bovine and porcine splits that are treated with a solution, minced, acidified and treated in a colloid mill. The collagen dispersion can be processed by a cylinder spinning system to spin a thread that may be coagulated in a bath, air dried, and wound on a bobbin. Electrospinning may subject a collagen-polymer solution to an electric field to induce the accumulation of a charge on the surface of a pendant drop. The charge accumulation generates a force that directly opposes the force produced by the surface tension of the drop that, above a critical value of electric field strength, can cause a charged jet to eject to form fine filaments. Additional information regarding electrospinning with collagen and a polyethylene oxide polymer may be described in Lei Huang, et al, "Engineered collagen-PEO nanofibers and fabrics," J. Biomater. Sci. Polymer Edn, Vol. 12, No. 9, pp. 979-993 (2001), which is incorporated by reference for all purposes. The filaments of collagen may then be cut into standardized lengths to form staple fibers. In some embodiments, the staple fibers of collagen may have a length between about 4 mm and about 6 mm.

The staple fibers formed from a supporting material may be formed from one or more of polyethylene oxide, alginate, polylactic aid, other bio-absorbable polymers, polyvinyl alcohol, polycapralactones, or polyamides. The staple fibers of the supporting material may be formed by producing filaments of the supporting material and cutting the filaments into standardized lengths. In some embodiments, the staple fibers of the supporting material may have a length between about 4 mm and about 6 mm.

The staple fibers of collagen and the staple fibers of the supporting material may be twisted together and carded to form the collagen fibers 126, 127. In some embodiments, the collagen content of the collagen fibers 126, 127 may be about 30% of the total content of the collagen fibers 126, 127. In other embodiments, the total collagen content of the collagen fibers 126, 127 may be between about 10% and about 50% of the total content of the collagen Fibers 126, 127. The remaining content of the collagen fibers 126, 127 may be the supporting material. For example, in some embodiments, the supporting material may be polyethylene oxide, and the polyethylene oxide may be between about 90% and about 50% of the total material content of the collagen fibers 126, 127. In some embodiments, the collagen fibers 126, 127 may be a string of collagen elements.

Referring to FIG. 1, negative pressure may be supplied to the tissue site 101 through the manifold 112. The manifold 112 may contract and compress the mesh 114 into a surface of the tissue site 101, and negative-pressure may be distributed to the tissue site 101 through the mesh apertures 130. The mesh 114 may readily absorb moisture from the tissue site 101. As the mesh 114 absorbs moisture from the tissue site 101, the collagen fibers 126, 127 of the mesh 114 may expand. The mesh apertures 130 may be sized so that negative pressure may continue to be distributed to the tissue site 101 through the mesh 114. The compression of the mesh 114 by the manifold 112 may also cause the mesh 114 to be pushed into the manifold 112 and may allow the manifold 112 to contact the surface of the tissue site 101, providing micro strain and delivering perfusion. The mesh 114 may not inhibit granulation, but swell and disperse into the manifold 112 to provide MMP modulation without restricting the flow of negative-pressure to the tissue site 101.

Figure 3:
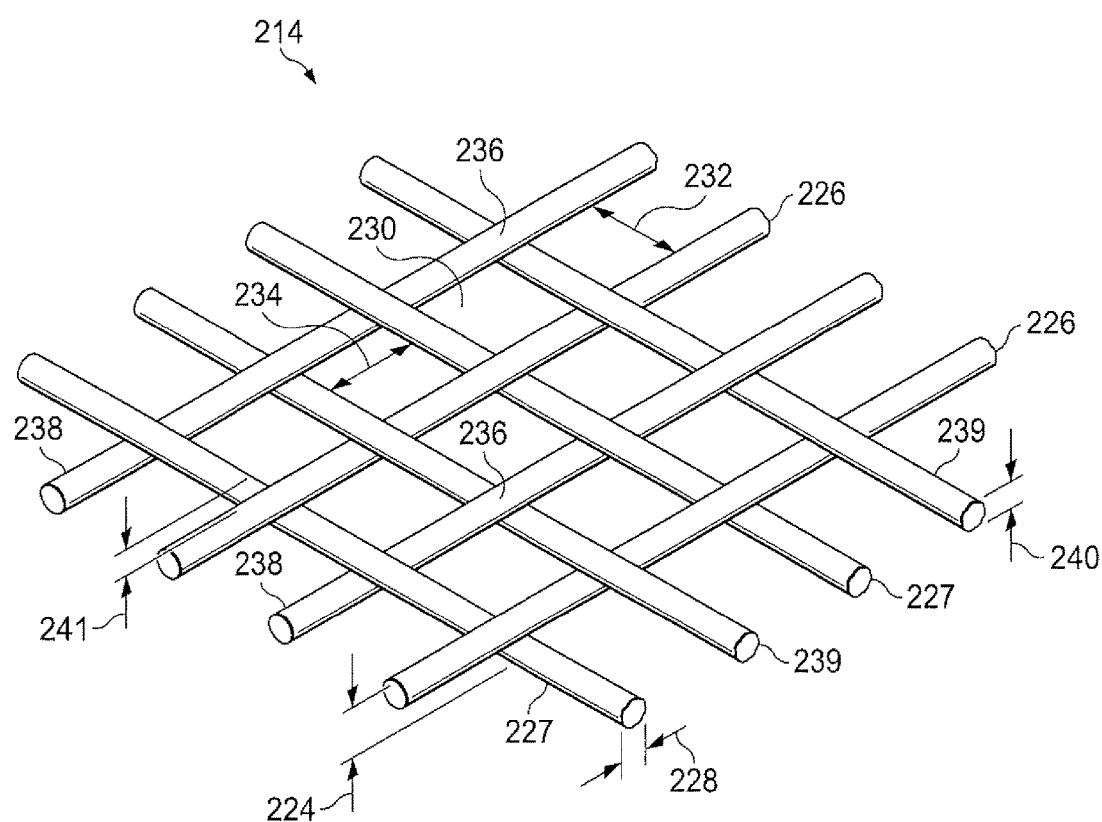
FIG. 3 is a perspective view, illustrating additional details that may be associated with another mesh of the negative-pressure therapy system of FIG. 1.

FIG. 3 is a perspective view of a portion of a mesh 214, illustrating additional details that may be associated with other example embodiments of the negative-pressure therapy system 100. The mesh 214 may be similar to and operate as described above with respect to the mesh 114. Similar elements may have similar reference numbers that are indexed to 200. As shown in FIG. 3, the mesh 214 may include a plurality of supporting fibers 238 and a plurality of collagen fibers 226. In some embodiments, the collagen fibers 226 and the supporting fibers 238 may be woven together to form a network or a mesh, such as the mesh 214. In some embodiments, the collagen fibers 226 and the supporting fibers 238 may be woven together so that the collagen fibers 226 and the supporting fibers 238 overlap at intersections 236. In some embodiments, the collagen fibers 226 and the supporting fibers 238 may be alternated. For example, a plurality of supporting fibers 238 may be laid in parallel rows, and a plurality of collagen fibers 226 may be laid with the plurality of supporting fibers 238 so that a collagen fiber 226 is between adjacent supporting fibers 238 to form a first layer of fibers 226, 238. A second layer of fibers 227, 239 having a similar makeup to the first layer of fibers 226, 238 may be woven with the first layer of fibers 226, 238 to produce the mesh 214 of FIG. 3.

The mesh 214 may include mesh apertures 230 formed by a distance 234 and a distance 232 between adjacent fibers. The mesh apertures 230 of the mesh 214 may have an average effective diameter between about 1 mm and about 5 mm. The mesh 214 of FIG. 3 may also include prominences 241 at the intersections 236 of the overlapping fibers, such as the collagen fibers 226, 227 and the supporting fibers 238, 239. The collagen fibers 226, 227 may also have a diameter 228.

Generally, a thickness 224 of the mesh 214, the collagen fibers 226, 227, the diameter 228, the mesh apertures 230, the distance 232, the distance 234, the intersections 236, and the prominence 241 may be similar to and operate as described above with respect to the mesh 114, the thickness 124 of the mesh 114, the collagen fibers 126, 127, the diameter 128, the mesh apertures 230, the distance 132, the distance 134, the intersections 136, and the prominence 141, respectively.

The supporting fibers 238, 239 may be fibers formed from the supporting material and having little or no collagen content. As described above, the supporting material may be one or more of polyethylene oxide, alginate, polylactic aid, other bio-absorbable polymers, polyvinyl alcohol, polycapralactones, or polyamides. The supporting fibers 238, 239 may be formed from a monofilament, a plurality of twisted monofilaments, a plurality of filaments, or a plurality of staple fibers. A monofilament may be a single filament. In some embodiments, a monofilament may be made from a single synthetic fiber of plastic, for example. Monofilaments may have a tensile strength related to a diameter of the monofilament and the type of material from which the monofilament is formed. A filament may be a fiber that is formed in a continuous or near-continuous length. Each of the supporting fibers 238, 239 may have a diameter 240. In some embodiments, the diameter 240 may be no greater than about 1 mm.

Figure 4:
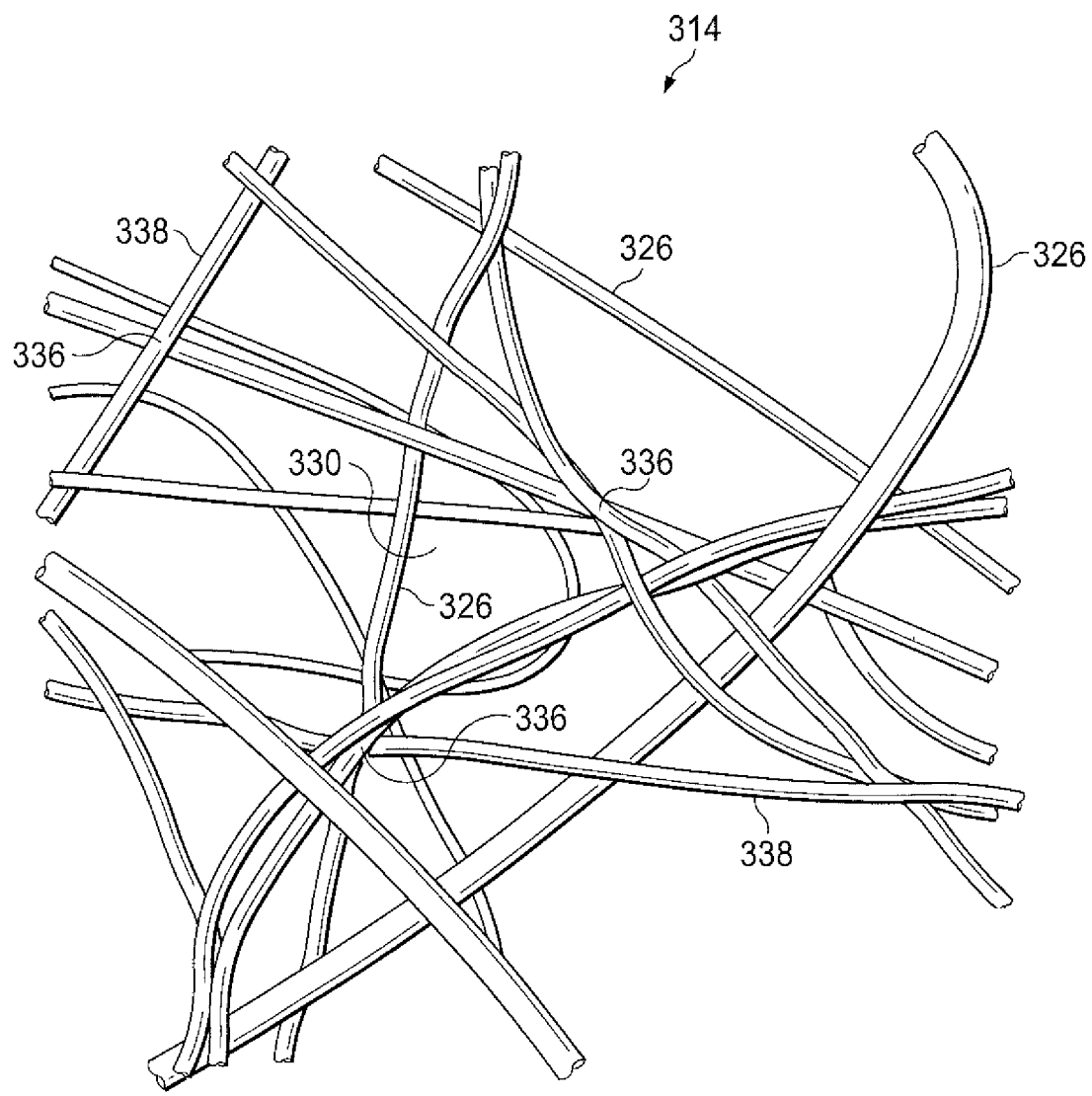
FIG. 4 is a schematic view, illustrating additional details that may be associated with another mesh of the negative-pressure therapy system of FIG. 1.

FIG. 4 is a schematic view of a portion of a mesh 314, illustrating additional details that may be associated with other example embodiments of the negative-pressure therapy system 100. The mesh 314 may be similar to and operate as described above with respect to the mesh 114. Similar elements may have similar reference numbers that are indexed to 300. In some embodiments, a plurality of collagen fibers 326 and a plurality of supporting fibers 338 may be formed into the non-woven mesh 314. For example, the collagen fibers 326 and the supporting fibers 338 may be dispersed on a conveyor belt, and spread in a uniform web by a wetlaid, an airlaid, or a carding/crosslapping process. The collagen fibers 326 and the supporting fibers 338 may be bonded thermally or by using a resin to form the mesh of the mesh 314. For example, the collagen fibers 326 and the supporting fibers 338 may overlap and form intersections 336 where the collagen fibers 326 and the supporting fibers 338 overlap with other fibers. The overlapping fibers of the mesh 314 may also form openings, such as mesh apertures 330. As shown in FIG. 4, the mesh apertures 330 may not be uniform in size. The mesh apertures 330 of the mesh 314 may have an average effective diameter between about 1 mm and about 5 mm. If the mesh apertures 330 are not uniform in size the average of the effective diameters of the mesh apertures 330 may be between about 1 mm and about 5 mm.

In some embodiments, the mesh 314 may also be formed in a spunlaid process having only the collagen fibers 326. Spunlaid nonwovens may be made in a continuous process by forming the collagen fibers 326 as described above. The collagen fibers 326 may be dispersed into a web by physical deflectors or with air streams without further cutting the collagen fibers 326.

Generally, a thickness of the mesh 314, the collagen fibers 326, a diameter of the collagen fibers 326, the mesh apertures 330, the intersections 336, the supporting fibers 338, and a diameter of the supporting fibers 338 may be similar to and operate as described above with respect to the mesh 114, the thickness 124 of the mesh 114, the collagen fibers 126, 127, the diameter 128, the mesh apertures 130, the intersections 136, the supporting fibers 238, and the diameter 240 of the supporting fibers 238 respectively.

Figure 5:
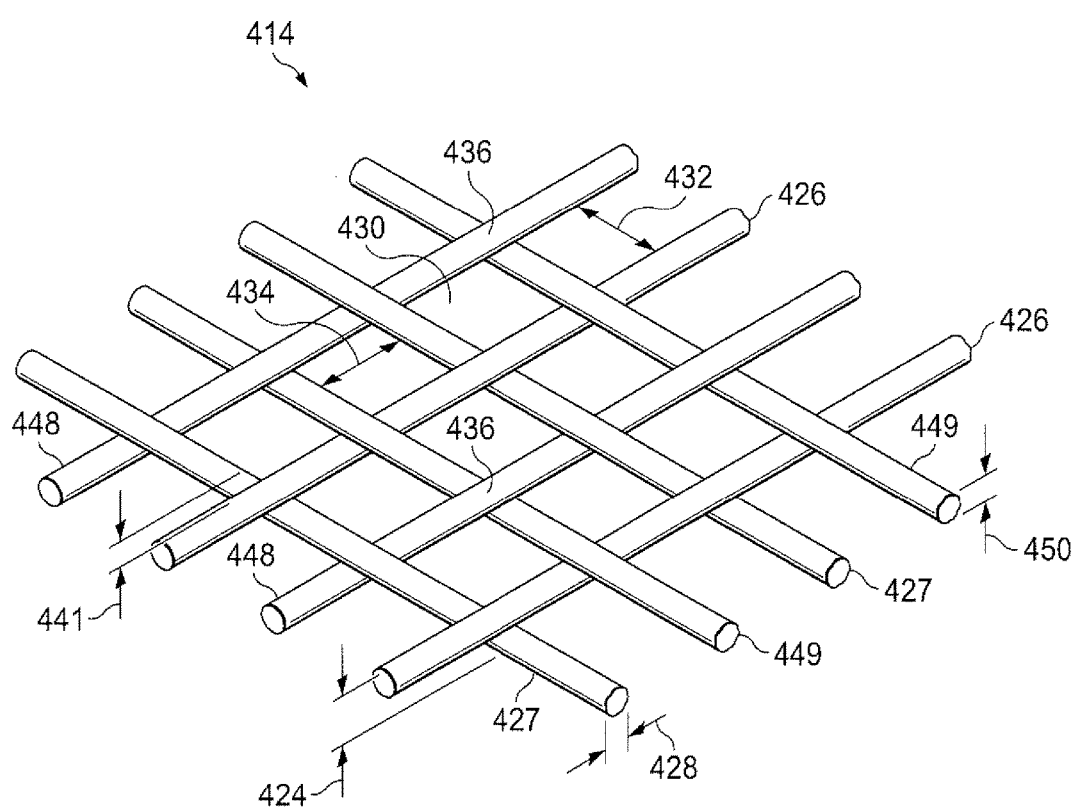
FIG. 5 is a perspective view, illustrating additional details that may be associated with another mesh of the negative-pressure therapy system of FIG. 1.

FIG. 5 is a perspective view of a portion of a mesh 414 having collagen and oxidized regenerated cellulose (ORC), illustrating additional details that may be associated with other example embodiments of the negative-pressure therapy system 100. The mesh 414 may be similar to and operate as described above with respect to the mesh 114. Similar elements may have similar reference numbers that are indexed to 400. As shown in FIG. 5, the mesh 414 may include a plurality of ORC fibers 448 and a plurality of collagen fibers 426. In some embodiments, the collagen fibers 426 and the ORC fibers 448 may be woven together to form a network or a mesh, such as the mesh 414. In some embodiments, the collagen fibers 426 and the ORC fibers 448 may be woven together so that the collagen fibers 426 and the ORC fibers 448 overlap at intersections 436. In some embodiments, the collagen fibers 426 and the ORC fibers 448 may be alternated. For example, a plurality of ORC fibers 448 may be laid in parallel rows, and a plurality of collagen fibers 426 may be laid with the plurality of ORC fibers 448 so that a collagen fiber 426 is between adjacent ORC fibers 448 to form a first layer of fibers 426, 448. A second layer of fibers 427, 449 having a similar makeup to the first layer of fibers 426, 438 may be woven with the first layer of fibers 426, 438 to produce the mesh 414 of FIG. 5.

The mesh 414 may include mesh apertures 430 formed by a distance 434 and a distance 432 between adjacent fibers. The mesh apertures 430 of the mesh 414 may have an average effective diameter between about 1 mm and about 5 mm. The mesh 414 of FIG. 5 may also include prominences 441 at the intersections 436 of the overlapping fibers, such as the collagen fibers 426, 427 and the ORC fibers 448, 449. The collagen fibers 426, 427 may also have a diameter 428.

Generally, a thickness 424 of the mesh 414, the collagen fibers 426, 427, the diameter 428, the mesh apertures 430, the distance 432, the distance 434, the intersections 436, and the prominence 441 may be similar to and operate as described above with respect to the mesh 114, the thickness 124 of the mesh 114, the collagen fibers 126, 127, the diameter 128, the mesh apertures 430, the distance 132, the distance 134, the intersections 136, and the prominence 141, respectively.

The ORC fibers 448, 449 may be fibers formed from the oxidized regenerated cellulose (ORC). ORC may be a regenerated polysaccharide polymer that may be extruded into fibers. In some embodiments, the ORC fibers 448, 449 may be fibers formed from oxidized cellulose. Oxidized cellulose may be a water insoluble derivative of cellulose produced from cellulose and an oxidizing agent that is extruded into fibers. In some embodiments, the ORC fibers 448, 449 may be a fiber formed from the supporting material having ORC that has been ground into a power, dispersed within or coating the fibers of the supporting material. The ORC fibers 448, 449 may be formed from a monofilament, a plurality of twisted monofilaments, a plurality of filaments, or a plurality of staple fibers. Each of the ORC fibers 448, 449 may have a diameter 450. In some embodiments, the diameter 450 may be no greater than about 1 mm.

In some embodiments, the ORC fibers 448, 449 may be disposed with the collagen fibers 426, 427 in a woven as illustrated in FIG. 5. In other embodiments, the ORC fibers 448, 449 may be disposed with the collagen fibers 426, 427 in a non-woven, similar to the mesh 314 of FIG. 4. In some embodiments, the ORC fibers 448, 449 may comprise about 45% of the mesh 414. The collagen fibers 427, 428 may comprise about 55% of the mesh 414. In some embodiments, about 45% of the non-supporting material of the mesh 414 may be ORC material, and about 55% of the non-supporting material of the mesh 414 may be collagen material.

As described above with respect to the mesh 114, negative pressure may be supplied to the tissue site 101 through the manifold 112, contracting and compressing the mesh 414 into a surface of the tissue site 101. Negative pressure may be distributed to the tissue site 101 through the mesh apertures 430. The mesh 414 may readily absorb moisture from the tissue site 101. As the mesh 414 absorbs moisture from the tissue site 101, the collagen fibers 426, 427 and the ORC fibers 448, 439 of the mesh 414 may expand. The mesh apertures 430 may be sized so that negative pressure may continue to be distributed to the tissue site 101 through the mesh 414. The compression of the mesh 414 by the manifold 112 may also cause the mesh 414 to be pushed into the manifold 112 and may allow the manifold 112 to contact the surface of the tissue site 101, providing microstrain and delivering perfusion. The mesh 414 may not inhibit granulation, but swell and disperse into the manifold 112 to provide MMP modulation, elastase modulation, and bacteria protease modulation without restricting the flow of negative-pressure to the tissue site 101.

The systems, apparatuses, and methods described herein may provide significant advantages. For example, a flexible and compatible method to apply and deliver the benefits of protease modulation and negative pressure therapy may be provided. In some embodiments, the mesh may provide MMP modulation without hindering the delivery of negative pressure to the tissue site and allowing creation of microstrain. In some embodiments, the mesh may also provide elastase and bacteria protease modulation in addition to MMP modulation. The mesh may also withstand heavy exudate flows without requiring removal. The mesh may be placed directly onto the tissue site and efficiently uses the available collagen while placing the collagen in direct contact with the tissue site. The mesh may be fully bisoabsorbable so could be placed in deep hard to access tissue sites where the removal of devices may not be desirable.

While shown in a few illustrative embodiments, a person having ordinary skill in the art will recognized that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A negative-pressure therapy system for modulating proteases in a tissue site, the system comprising:
 a modulating layer including a plurality of collagen fibers reinforced with a supporting material and intersecting with each other to form a network of collagen fibers having a plurality openings;

wherein the openings of the plurality of openings have an average effective diameter between about 0.5 mm and about 5 mm to permit the flow of negative pressure through the network;
a manifold configured to be positioned adjacent the network;
a cover configured to be positioned over the manifold and the network and coupled to tissue adjacent the tissue site to form a sealed space; and
a negative-pressure source configured to be fluidly coupled to the manifold to provide negative pressure to the sealed space through the manifold and the network.

2. The method of claim 1, wherein the openings have an average area between about 0.2 mm$^2$ and about 20.0 mm$^2$.

3. The system of claim 1, wherein the openings are generally circular in shape and have an average diameter between about 1 mm and about 2.5 mm.

4. The system of claim 1, wherein the collagen fibers have a diameter of less than about 1 millimeter.

5. The system of claim 1, wherein the collagen fibers have a diameter of between about 1 micron and 50 microns.

6. The system of claim 1, wherein the network has a thickness between about 5 microns and about 2 millimeters.

7. The system of claim 1, wherein the network has a thickness of about 25 microns.

8. The system of claim 1, wherein the collagen fibers have a collagen content between about 10% and about 50% of the total material of the collagen fiber.

9. The system of claim 1, wherein the collagen fibers comprise a string of collagen elements.

10. The system of claim 1, wherein the supporting material comprises supporting fibers.

11. The system of claim 10, wherein the supporting fibers are twisted with the plurality of collagen fibers.

12. The system of claim 10, wherein the supporting fibers support separate collagen elements to form the plurality of collagen fibers.

13. The system of claim 12, further comprising a plurality of supporting fibers operatively coupled to the plurality of collagen fibers.

14. The system of claim 12, wherein the plurality of supporting fibers and the plurality of collagen fibers are woven together.

15. The system of claim 12, wherein the supporting fibers are water soluble.

16. The system of claim 12, wherein the supporting fibers are biodegradable.

17. The system of claim 12, wherein the plurality of collagen fibers and the plurality of supporting fibers have a collagen content between about 10% and about 50% of the modulating layer.

18. The system of claim 12, wherein the collagen fibers and supporting fibers are non-woven.

19. The system of claim 1, wherein the collagen fibers comprise:
staple fibers formed from collagen; and
staple fibers formed from the supporting material;
wherein the staple fibers formed of collagen and the staple fibers formed of the supporting material are twisted together to form the collagen fibers.

20. The system of claim 19, wherein the supporting material comprises one or more selected from a group consisting of: polyethylene oxide, alginate, polylactic acid, polyvinyl alcohol, polycapralactones, and polyamides.

21. The system of claim 19, wherein a length of the staple fibers formed from collagen is between about 4 mm and about 6 mm.

22. The system of claim 19, wherein the collagen fibers have a collagen content between about 10% and about 50% of the total material of the collagen fiber.

23. The system of claim 1, further comprising a plurality of oxidized regenerated cellulose fibers intersecting the collagen fibers to form the network having the plurality of openings.

24. The system of claim 23, wherein about 45% of the network comprises oxidized regenerated cellulose fibers.

25. The system of claim 23, wherein about 55% of the network comprises collagen fibers.

* * * * *